(12) United States Patent
Wieckhusen et al.

(10) Patent No.: US 8,227,488 B2
(45) Date of Patent: *Jul. 24, 2012

(54) INJECTABLE DEPOT FORMULATION COMPRISING CRYSTALS OF ILOPERIDONE

(75) Inventors: Dierk Wieckhusen, Binzen (DE); Alexandra Glausch, Weil am Rhein (DE); Markus Ahlheim, Staufen (DE)

(73) Assignee: Novartis AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 13/401,310

(22) Filed: Feb. 21, 2012

(65) Prior Publication Data

US 2012/0156264 A1    Jun. 21, 2012

Related U.S. Application Data

(63) Continuation of application No. 13/106,417, filed on May 12, 2011, which is a continuation of application No. 12/254,925, filed on Oct. 21, 2008, now abandoned, which is a continuation of application No. 10/521,064, filed as application No. PCT/EP03/07619 on Jul. 14, 2003, now abandoned.

(30) Foreign Application Priority Data

Jul. 15, 2002  (GB) .................................. 0216416.8

(51) Int. Cl.
| A01N 43/00 | (2006.01) |
| A01N 43/40 | (2006.01) |
| A61K 31/553 | (2006.01) |
| A61K 31/554 | (2006.01) |
| A61K 31/445 | (2006.01) |
| C08J 9/28 | (2006.01) |
| C07D 211/22 | (2006.01) |
| C07D 261/20 | (2006.01) |

(52) U.S. Cl. .................... 514/320; 514/211.13; 514/321; 521/64; 546/197; 546/198

(58) Field of Classification Search ................ 435/6, 29; 514/211.13, 321; 521/64; 546/197, 198
See application file for complete search history.

(56) References Cited

U.S. PATENT DOCUMENTS

| 4,780,460 | A | 10/1988 | Dusterlerg et al. |
| 5,364,866 | A | 11/1994 | Strupczewski et al. |
| 5,460,956 | A | 10/1995 | Reichert et al. |
| 5,538,739 | A | 7/1996 | Bodmer et al. |
| 5,741,485 | A | 4/1998 | Reichert et al. |
| 5,776,963 | A | 7/1998 | Strupczewski et al. |
| 6,368,632 | B1 | 4/2002 | Mesens et al. |
| 6,555,544 | B2 | 4/2003 | Francois et al. |
| 2002/0045582 | A1 | 4/2002 | Margolin et al. |
| 2005/0250813 | A1 | 11/2005 | Wieckhusen et al. |

FOREIGN PATENT DOCUMENTS

| CA | 2327883 | 4/1999 |
| CN | 1137756 | 12/1996 |
| EP | 0402644 A1 | 5/1990 |
| EP | 0307619 A2 | 7/2003 |
| GB | 2145422 | 8/1984 |
| GB | 0216416 | 7/2002 |
| JP | 60076531 | 6/1985 |
| WO | 9511680 | 5/1995 |
| WO | 9854186 A1 | 12/1998 |
| WO | 0023057 | 4/2000 |
| WO | WO0192457 A1 | 12/2001 |
| WO | 03020707 A1 | 3/2003 |
| WO | 2004006886 A2 | 1/2004 |

OTHER PUBLICATIONS

Pieters et al., "Sustained Release Properties of an Intra-adiposely Administered Dapsone Depot Injection," International Journal of Leprosy, vol. 54, No. 3 (Sep. 9, 2007), pp. 383-388.
Schilffarth, "About the symptomatic treatment of hay fever with a new depot crystal suspension," Therapie der Gegenwart 117 (1978), pp. 797-807 (English translation version).
Miescher et al., "Depot Effect of crystal suspensions of female sex hormones (Ovocyclin—and Lutocyclin [progesterone]—crystal ampoules)," Helv. Physiol. Acta 2 (Jul. 1944), pp. 515-532 (English translation version).
Blagden et al., "Crystal engineering of active pharmaceutical ingredients to improve solubility and dissolution rates," Advanced Drug Delivery Reviews 59 (May 2007), pp. 617-630.
Shekunov et al., "Crystallization processes in pharmaceutical technology and drug delivery design," Journal of Crystal Growth 211 (2000), pp. 122-136.
Vippagunta et al., "Crystalline solids," Advanced Drug Delivery Reviews 48 (2001), pp. 3-26.
Rodriguez-Spong et al., "General principles of pharmaceutical solid polymorphism: a supramolecular perspective," Advanced Drug Delivery Reviews 56 (2004), pp. 241-274.
Singhal et al., "Drug polymorphism and dosage form design: a practical perspective," Advanced Drug Delivery Reviews 56 (2004), pp. 335-347.
Rothele et al., "Standards in Laser Diffraction," Proc. 5th European Symposium Particle Characterization, Mar. 1992, pp. 625-642.
Corey et al., "A Stable and easily prepared catalyst for the enantioselective reduction of ketones. Applications to multistep syntheses," Sep. 1987, S. J. Am. Chem. Soc., 109, pp. 7925-7926.
Kelleher et al. "Advances in Atypical Antipsychotics for the Treatment of Schizophrenia," 2002, CNS Drugs, 16 (4), pp. 249-261.
Mutlib et al., "Picogram determination of iloperidone in human plasma by solid-phase extraction and by high-performance liquid chromatography-selected-ion monitoring electrospray mass spectrometry," Feb. 1995, Journal of Chromatography B, 669, pp. 237-246.

(Continued)

*Primary Examiner* — Johann Richter
*Assistant Examiner* — Luke Karpinski
(74) *Attorney, Agent, or Firm* — Hoffman Warnick LLC; Drew Holmes (57) ABSTRACT

An injectable depot formulation comprising crystals having structure (I) wherein R is (FII) and the X50 value of the crystals is from 1 to 200 microns. Depot formulations containing crystals of iloperidone or its metabolites have the following advantages: (i) release of the crystals in plasma can be correlated with the size of the crystals; (ii) absorption of the crystals in plasma can be correlated with the size of the crystals; (iii) the particle size of the crystals can be controlled by crystal engineering and/or milling; and (iv) the crystals are stable upon storage, and stable to sterilization procedures, such as gamma irradiation.

17 Claims, 4 Drawing Sheets

OTHER PUBLICATIONS

Patent Cooperation Treaty, International Preliminary Examination Report for Application No. PCT/EP03/07619 dated Jan. 12, 2005, 2 pages.
European Patent Office, Letter from the Opponent for Application No. EP1523335 dated Nov. 24, 2009, 4 pages.
European Patent Office, Notice of Opposition to a European Patent for Application No. EP1523335 dated Sep. 20, 2007, 518 pages.
European Patent Office, Response to Notice of Opposition for Application No. EP1523335 dated Jul. 2, 2008, 49 pages.
Heuer et al- "Results Obtained with a New Instrument for the Measurement of Particle Size Distributions from Diffraction Patterns," Oct. 1984, Part. Charact. 2, pp. 7-13.
Corbett et al., "Effects of Atypical Antipsychotic Agents on Social Behavior in Rodents," 1993, Pharmacology Biochemistry and Behavior, vol. 45, pp. 9-17.
Patent Cooperation Treaty, Notification of Transmittal of the International Search Report of the Declaration for Application No. PCT/EP03/07619 dated Jan. 8, 2004, 6 pages.
Japanese Patent Office, Official Action for Application No. 2004-520629 dated Dec. 8, 2009, 3 pages.
Japanese Patent Office, Final Rejection for Application No. 2004-520629 dated Jun. 29, 2010, 3 pages.
Horioka, "Injection," Nanzando, 1995, pp. 23-25.
Okano, "New Pharmacy," 3rd Edition, 1987, pp. 76-81.
Karpinski, Office Action Communication for U.S. Appl. No. 10/521,064 dated Apr. 28, 2008, 21 pages.
Karpinski, Office Action Communication for U.S. Appl. No. 10/521,064 dated Oct. 12, 2007, 13 pages.
Karpinski, Office Action Communication for U.S. Appl. No. 12/254,925 dated Dec. 22, 2010, 15 pages.
Karpinski, Office Action Communication for U.S. Appl. No. 12/254,925 dated Sep. 17, 2010, 26 pages.
Peters, Australian Patent Application 2003281154, Examiner's First Report, Nov. 7, 2005, 2 pages.
Australian Patent Application 2003281154, Notice of Acceptance, Oct. 3, 2006, 4 pages.
Young, Canadian Patent Application No. 2,492,467, Office Action, Aug. 20, 2008, 2 pages.
Canadian Patent Application No. 2,492,467, Notice of Allowance, Jun. 18, 2009, 2 pages.
European Patent No. 03756455.6, Decision to Grant, Nov. 23, 2006, 1 page.
Harris, New Zealand Patent Application No. 537598, Notice of Acceptance of Complete Specification, Jul. 5, 2006, 1 page.
Handley, Application No. GB 0216416.8, Search Report under Section 17, Dec. 18, 2002, 1 page.
Karpinski, U.S. Appl. No. 12/254,925, Advisory Action, Mar. 11, 2011, 4 pages.
Karpinski, U.S. Appl. No. 12/254,925, Notice of Panel Decision from Pre-Appeal Brief Review, Apr. 5, 2011, 3 pages.
Sathapana Kongsamut et al., Iloperidone binding to human and rate dopamine and 5-HT receptors, European J. of Pharmacology 317, pp. 417-429 (1996).
Hesselink, Current Opinion in Central and Peripheral Nervous System Investigational Drugs, 2000, Abstract, 1 page.
Mucke, et al., Iloperidone: Antipsychotic, dopamine D2 antagonist, 5-HT2A antagonist, Drugs of the Future, 25(1), pp. 29-40 (2000).
Karpinski, Office Action Communication for U.S. Appl. No. 13/106,417 dated May 10, 2012, 21 pages.

INJECTABLE DEPOT FORMULATION COMPRISING CRYSTALS OF ILOPERIDONE

CROSS REFERENCE TO RELATED APPLICATIONS

This application is a continuation application of U.S. patent application Ser. No. 13/106,417, filed May 12, 2011, which is a continuation of U.S. patent application Ser. No. 12/254,925, filed Oct. 21, 2008 now abandoned; which is a continuation of U.S. patent application Ser. No. 10/521,064, filed Jan. 12, 2005 now abandoned; which is a 35 U.S.C. §371 application claiming the benefit of PCT Patent Application Serial No. PCT/EP03/07619, filed Jul. 14, 2003; which in turn claims the benefit of British Patent Application No. GB0216416, filed Jul. 15, 2002, each of which is incorporated herein.

FIELD OF THE INVENTION

This invention relates to an injectable depot formulation comprising crystals of iloperidone or its metabolite wherein the release and absorption of the crystals in plasma can be correlated with the crystal size.

BACKGROUND OF THE INVENTION

The controlled release of an active agent from poly(d,l-lactide-co-glycolide) microspheres and the general status of such lactide use is discussed in the article "Controlled Release of a Luteininizing Hormone-Releasing Hormone Analogue from Poly(d,l-lactide-co-glycolide) Microspheres" by L. M. Sanders et al., J. of Pharm. Sci., 73, No. 9, September (1994).

Microencapsulated depot formulations of iloperidone and a poly-glycolide polylactide glucose star polymer are disclosed in U.S. Patent Application Nos. 60/339,036, filed Oct. 30, 2001, and 60/339,037, filed Oct. 30, 2001.

U.S. Pat. No. 5,955,459 describes compositions for treating schizophrenia containing conjugates of a fatty acid and iloperidone. A preferred fatty acid is cis-docosahexanoic acid.

It would be advantageous to develop an iloperidone or its metabolite depot formulation that is as chemically-pure as possible, and which is stable to sterilization procedures, such as gamma irradiation. Furthermore, the depot formulation should provide a reliable, reproducible and constant plasma concentration profile of iloperidone or its metabolite following administration to a patient.

SUMMARY OF THE INVENTION

The present invention provides an injectable depot formulation comprising crystals of iloperidone or its metabolite or a pharmaceutically acceptable salt, hydrate, solvate, polymorph and stereoisomer thereof, wherein the mean particle size ($X_{50}$ value) of the crystals is from 1 to 200 microns.

According to another aspect the invention provides an injectable depot formulation comprising crystals having Structure (I)

wherein R is and the $X_{50}$ value of the crystals is from 1 to 200 microns.

According to a further aspect the invention provides crystals of iloperidone or its metabolite or a pharmaceutically acceptable salt, hydrate, solvate, polymorph and stereoisomer thereof, wherein the $X_{50}$ value of the crystals is from 1 to 200 microns.

The present inventors have unexpectedly determined that depot formulations containing crystals of iloperidone or its metabolite have the following advantages: (i) release of the crystals in plasma can be correlated with the size of the crystals; (ii) absorption of the crystals in plasma can be correlated with the size of the crystals; (iii) the particle size of the crystals can be controlled by crystal engineering and/or milling; and (iv) the crystals are stable upon storage, and stable to sterilization procedures, such as gamma irradiation.

DESCRIPTION OF THE INVENTION

Iloperidone is 1-[4-[3-[4-(6-fluoro-1,2-benzisoxazol-3-yl)-1-piperidinyl]propoxy]-3-methoxyphenyl]ethanone. As used herein, "iloperidone" includes any salts, hydrates, solvates, polymorphs such as amorphous polymorphs, and/or stereoisomers thereof. The metabolite of iloperidone is 1-[4-[3-[4-(6-fluoro(d)isoxazol-3-yl)-piperidinyl]propoxy]-3-methoxyphenyl]ethanol. As used herein, "metabolite of iloperidone" includes any salts, hydrates, solvates, polymorphs such as amorphous polymorphs, and/or stereoisomers thereof.

Preferably, the crystals have Structure (I)

wherein R is

It is noted that when R is the crystals may exist as either the (R) or (S) enantiomer, or as a racemic mixture thereof. The (S) enantiomer has Structure II The (R) enantiomer has Structure (III)

The crystals may be in the form of needles, trigonal forms, tetragonal forms, flat rod shaped, cubes, parallelepipeds, or plate-like. The mean particle size ($X_{50}$ value) of the crystals is preferably from about 1 to about 200 microns, more preferably 10 to 170 microns, whereby application of the depot formulation to a patient can be carried out using a standard gauge (typically 18 or 20 gauge) needle. Most preferably, the mean particle size ($X_{50}$ value) of the crystals is from 15 to 70 microns.

The crystals may be prepared by crystal growth or engineering directly to a desired crystal size. In the alternative, the crystals may be prepared to a larger crystal size than is desired in the depot formulations. In such a situation, the crystals may be milled or ground to achieve crystals having a size in the desired range. Such a milling step, for example, is important for achieving the desired crystal size distribution. In principle any mill can be used, for example, a pinmill. Following milling, the crystals may optionally be passed through a screen stack or sieve with crystals of the desired size retained white the crystals failing outside of the desired range (either too small or too large) are discarded.

It is also within the scope of the invention to provide the depot formulations of the invention as suspensions in a suitable vehicle. Aqueous suspensions are preferred such as the crystals suspended in water. The present inventors have determined that in the case of a suspension, the crystals are preferable administered with one or more additional ingredients.

Additional ingredients which may be used in the depot formulations of the invention include natural and/or artificial ingredients which are commonly used to prepare pharmaceutical compositions. Examples of additional ingredients include a surfactant, solubilizer, emulsifier, preservative, isotonicity agent, dispersing agent, wetting agent, filler, solvent, buffer, stabilizer, lubricant, and thickening agent. A combination of additional ingredients may also be used. Preferred additional ingredients are a surfactant, isotonicity agent, and thickening agent. Generally, such ingredients and their concentrations in parenteral formulations are known to those skilled in the art, and thus, only examples of the preferred additional ingredients are described. The depot formulations of the invention should not be limited to the following examples of preferred additional ingredients.

Examples of surfactants include: sorbitan fatty acid esters such as sorbitan trioleate, phosphatides such as lecithin, acacia, tragacanth, polyoxyethylated sorbitan monooleate end other ethoxylated fatty acid esters of sorbitan, polyoxyalkylene derivatives of propylene glycol, such as those available under the trademark PLURONICS, especially PLURONICS F68; polyoxyethylated fats, polyoxyethylated oleotriglycerides, linolizated oleotriglycerides, polyethylene oxide condensation products of fatty alcohols, alkylphenols or fatty acids or 1-methyl-3-(2-hydroxyethyl)imidazolidone-(2). As used herein, "polyoxyethylated" means that the substances in question contain polyoxyethylene chains, the degree of polymerization of which generally is between 2 and 40, and preferably, between 10 and 20. A preferred surfactant is a polyoxyalkylene derivative of propylene glycol, such as PLURONICS F68 which is available from BASF.

The amount of surfactant in the depot formulations of the invention is in the range known in the art for parenteral formulations, preferably from about 0.5 to about 10 mg/mL.

Examples of thickening agents include: croscarmellose sodium, sodium carboxymethyl cellulose, and hydroxypropyl cellulose. A preferred thickening agent is sodium carboxymethyl cellulose.

The amount of thickening agent in the depot formulations of the invention is in the range known in the art for parenteral formulations, preferably from about 2 to about 25 mg/mL.

Examples of isotonicity agents which may impart tonicity to the depot formulations to prevent the net flow of water across a cell membrane, include: salts such as sodium chloride; sugars such as dextrose, mannitol, and lactose. Mannitol is a preferred isotonicity agent.

The amount of isotonicity agent in the depot formulations of the invention is in the range known in the art for parenteral formulations.

The amount of iloperidone or its metabolite in the depot formulations will vary depending upon the severity of the condition to be treated. The depot formulations of the invention are preferably injectable and may be administered by intramuscular or subcutaneous injection. The depot formulations administered by injection provide an effective treatment of diseases over an extended period, for example, from about 2 to about 8 weeks. The depot formulation allows a controlled release of iloperidone or its metabolite by dissolution of the crystals, and therefore, steady state levels of the iloperidone or its metabolite are obtained over the extended period.

The amount of iloperidone or its metabolite administered in one injection is preferably from about 10 mg to about 1000 mg. More preferably, the amount of iloperidone or its metabolite administered in one injection is from about 100 mg to about 750 mg.

In one embodiment of the invention, the crystals of defined size are filled into a glass vial, purged with nitrogen and sealed with a rubber stopper. The vial may be terminal sterilized by gamma irradiation, preferably, in a range of 25-35 kGy or manufactured under aseptic conditions.

In one embodiment of the invention, the iloperidone crystals are injected into the body.

In one embodiment of the invention, the crystals of the metabolite of iloperidone are injected into the body.

In another embodiment of the invention, the iloperidone crystals we suspended in water, and the suspension is injected into the body.

In another embodiment of the invention, the crystals of the metabolite of iloperidone are suspended in water, and the suspension is injected into the body.

The depot formulation of the invention is useful for treating central nervous system disorders, for example, psychotic disorders such as schizophrenia. The invention also provides a package comprising a container containing the depot formulation and instructions for using the depot formulation for treating schizophrenia in a patient.

The following examples further describe the materials and methods used in carrying out the invention. The examples are not intended to limit the invention.

EXAMPLE 1

Preparation of 1-[4-[3-[4-(6-fluoro-1,2-benzisoxazol-3-yl)-1-piperidinyl]propoxyl]-3-methoxyphenyl]ethanone having the structure Into a 2 L Erlenmeyer flask with magnetic stirrer and reflux cooler under nitrogen atmosphere and an external temperature of 20-25° C., 250 g of iloperidone and 1050 g of butylacetate, were added. The light brown suspension was heated to an internal temperature of 80° C. until a brownish solution was formed. The solution was filtered over Cellflock into a preheated 2.5 L glass vessel with a blade-stirrer and reflux-cooler under nitrogen atmosphere. The Erlenmeyer flask and filter were washed with warm butylacetate (ca. 70° C.). The brownish solution was reheated to an internal temperature of 80° C. and stirred for 5 to 10 minutes. The solution was cooled with 0.75 K/min to an internal temperature of 65° C. and seeded with 2.5 g of iloperidone milled, which was suspended and ultrasonicated in 7.5 g of butylacetate.

The suspension was cooled to an internal pressure of 0° C. with a rate of 0.25 K/min and stirred for 2 to 12 hours at an internal temperature of 0° C. The suspension was filtered over a glass nutsche (0=110 mm) for 15 seconds. The filter cake (cake thickness=4 cm) was flushed with motherliquor end 275 g of cold butylacetate (0° C.) in two portions.

Iloperidone, 315 g, was obtained as wet, light brownish filtercake. The wet product was dried at an external temperature of 50-60° C. under a vacuum of less than 2 mbar for about 16-24 hours. Iloperidone, 238.3 g, was obtained. Theoretical yield was determined to be 94.4%.

EXAMPLE 2

The iloperidone crystals prepared in Example 1, 120 mg, having a particle size $X_{50}$=32 µm were reconstituted with 1 ml of a mixture containing sodiumcarboxymethylcellulose, Pluronics F68, and mannitol, by shaking resulting in a homogeneous suspension. The suspension was withdrawn from the vial with a syringe and injected into rabbits.

EXAMPLE 3

The iloperidone crystals prepared in Example 1, 850 mg, having a particle size $X_{50}$=15 µm were reconstituted with 2 ml of a mixture containing sodiumcarboxymethylcellulose, Pluronics F68, and mannitol, by shaking or swirling until a homogeneous suspension was obtained. This pastelike suspension was withdrawn from the vial with a syringe and injected into rabbits.

EXAMPLE 4

The iloperidone crystals prepared in Example 1, 850 mg, having a particle size $X_{50}$=51 µm were reconstituted with 2 ml of a mixture containing sodiumcarboxymethylcellulose, Pluronics F68, and mannitol, by shaking resulting in a homogeneous suspension. The suspension was withdrawn from the vial with a syringe and injected into rabbits.

EXAMPLE 5

Figure 1:
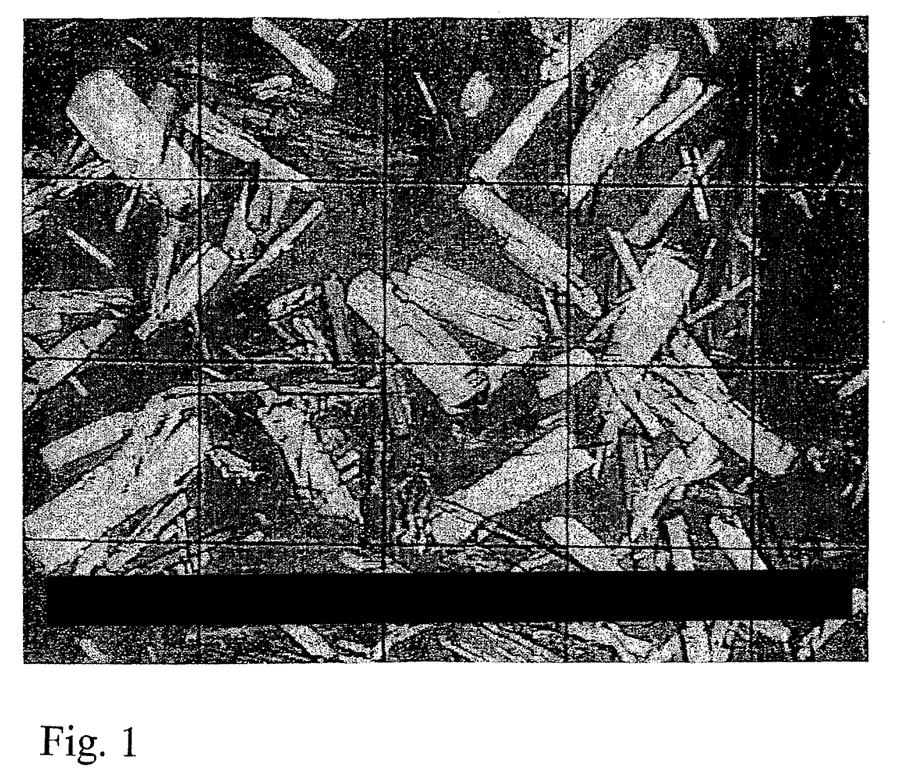
FIG. 1 is a photomicrograph of iloperidone crystals wherein 1 grid is equal to 100 microns.
Figure 2:
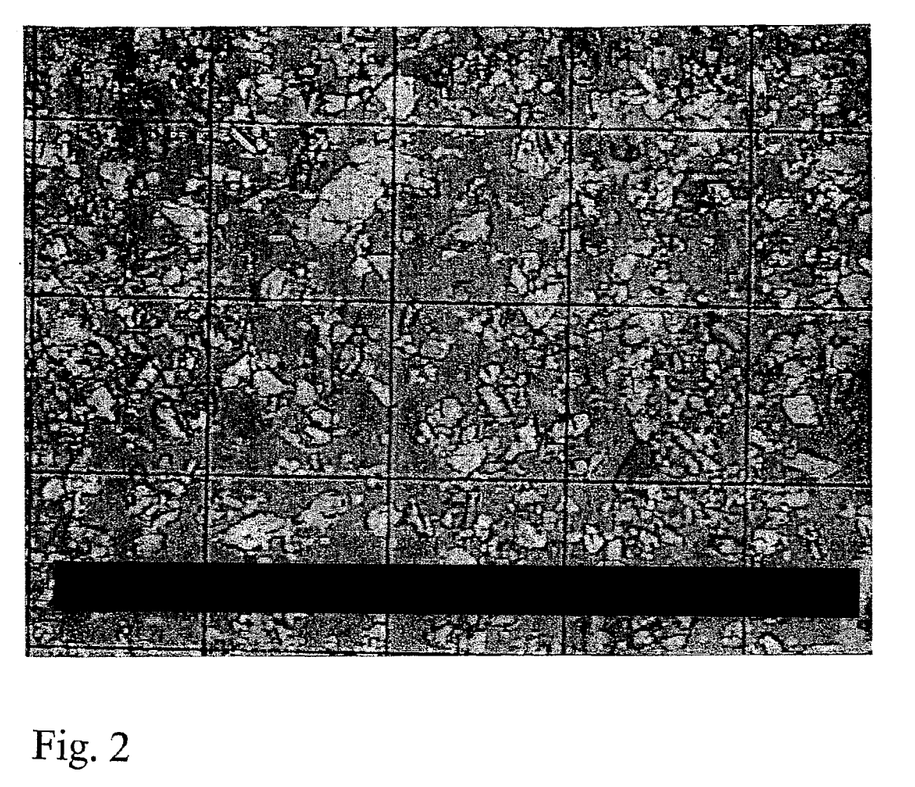
FIG. 2 is a photomicrograph of iloperidone crystals after milling wherein 1 grid is equal to 250 microns.
Figure 3:
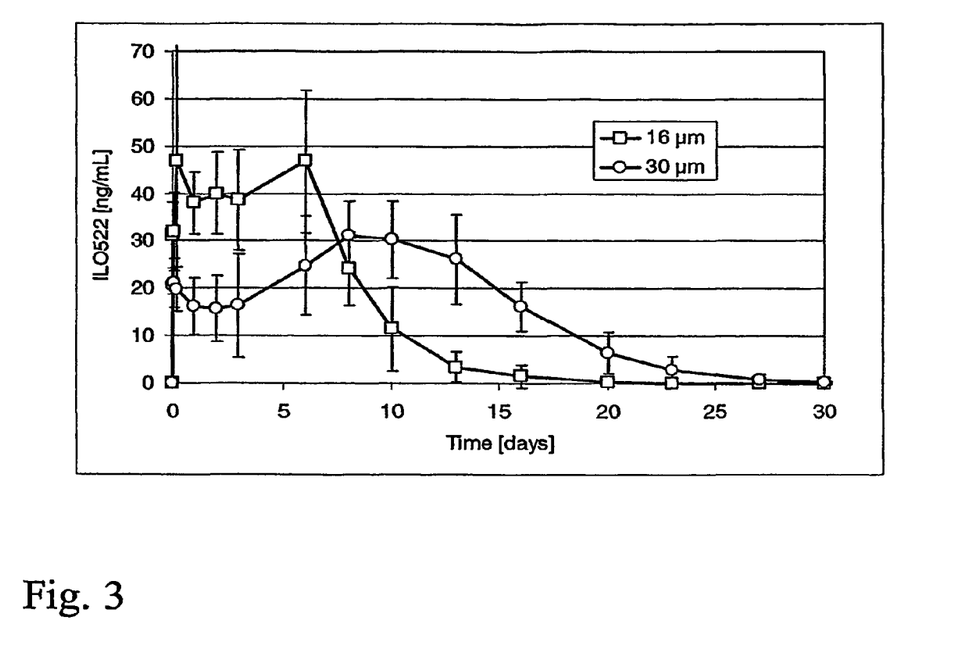
FIG. 3 is a graph of mean plasma concentrations in female rabbits of an iloperidone crystal depot formulation having an $X_{50}$ value of 16 microns and 30 microns over a period of time.

Regarding the drawings, FIG. 3 is a graph of mean plasma concentrations in female rabbits of an iloperidone crystal depot formulation having an $X_{50}$ value of 16 microns and 30 microns over a period of time. The formulations were dose normalized to 20 mg of iloperidone per kg of each rabbit. Each formulation was injected into six rabbits. FIG. 3 shows that the depot formulations prepared with iloperidone crystals having a $X_{50}$=16 remained in the plasma of the rabbits for at least 16 days. The depot formulations prepared with iloperidone crystals having a $X_{50}=30$ remained in the plasma of the rabbits for at least 25 days. The mean dose normalized pharmacokinetic parameters of iloperidone in plasma for each crystal size are summarized in Table I.

TABLE I

| Formulation | Actual dose Iloperidone [mg/kg] mean | $C_{max,d}$ [ng/mL] mean | $T_{max,d}$ [d] median |
|---|---|---|---|
| 16 um | 16.7 | 53.2 | 6 |
| 30 um | 17.0 | 35.3 | 9 |

The results in Table I and graph of FIG. 3 clearly show that the mean plasma concentration of iloperidone can be correlated with the particle size of the iloperidone crystals.

EXAMPLE 6

Figure 4:
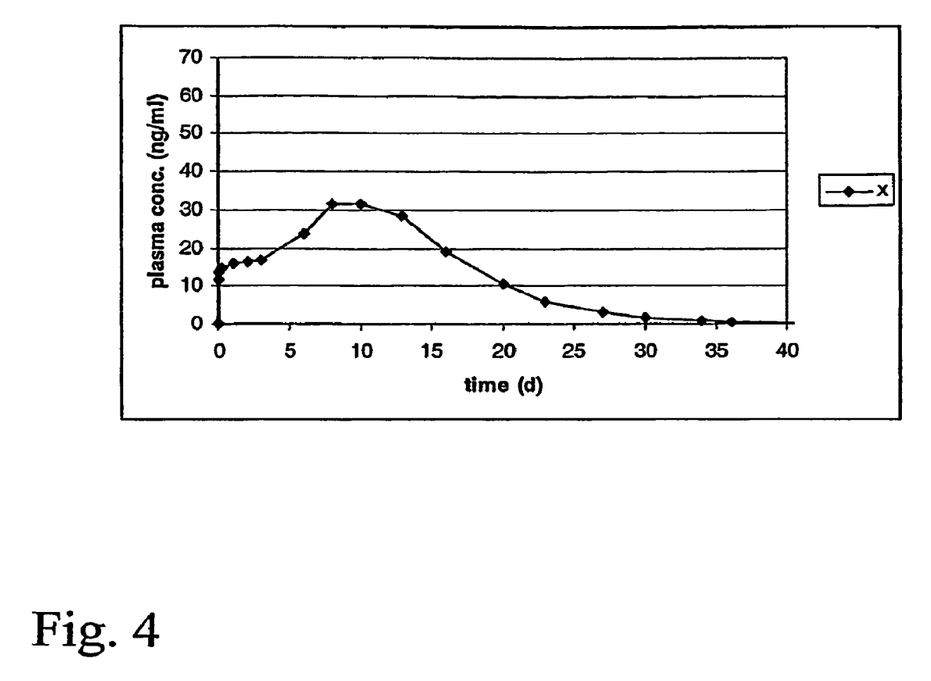
FIG. 4 is a graph of mean plasma concentrations in female rabbits of an iloperidone crystal depot formulation having an $X_{50}$) value of 170 microns over a period of time.

Regarding the drawings. FIG. 4 is a graph of mean plasma concentrations in female rabbits of an iloperidone crystal depot formulation having an $X_{50}$ value of 170 microns over a period of time. The formulations were dose normalized to 20 mg of iloperidone per kg of each rabbit. The formulation was injected into six rabbits. FIG. 4 shows that the depot formulations prepared with iloperidone crystals having a $X_{50}=170$ microns remained in the plasma of the rabbits for at least 30 days. The mean dose normalized pharmacokinetic parameters of iloperidone in plasma are summarized in Table II.

TABLE II

| Formulation | Actual dose Iloperidone (mg/kg) Mean | $C_{max,a}$ [ng/mL] | $T_{max,a}$ [d] (median) |
|---|---|---|---|
| 170 um | 15.7 ± 1.9 | 37.4 ± 11.2 | 10.5 |

Depot formulations containing crystals of iloperidone or its metabolite have the following advantages: (i) release of the crystals in plasma can be correlated with the size of the crystals; (ii) absorption of the crystals in plasma can be correlated with the size of the crystals; (iii) the particle size of the crystals can be controlled by crystal engineering and/or milling; and (iv) the crystals are stable upon storage, and stable to sterilization procedures, such as gamma irradiation.

While the invention has been described with particular reference to certain embodiments thereof. It will be understood that changes and modifications may be made by those of ordinary skill within the scope and spirit of the following claims:

We claim:

1. An injectable depot formulation comprising about 100 to about 750 mg of crystals of iloperidone or of its metabolite, suspended in an aqueous suspension, wherein the $X_{50}$ value of the crystals is from 1 to 200 microns, which formulation, following administration to a patient suffering a psychotic disorder by subcutaneous or intramuscular injection, provides an effective treatment amount over a period of about 2 to about 8 weeks.

2. An injectable depot formulation according to claim 1 comprising crystals having Structure (I)

wherein R is wherein the aqueous suspension is water, and the $X_{50}$ value of the crystals is from 1 to 200 microns.

3. The depot formulation according to claim 2 wherein the crystals have Structure (II)

4. The depot formulation according to claim 2 wherein the crystals have Structure (III)

5. The depot formulation according to claim 2 wherein the crystals are a combination of crystals having Structure (II)

and crystals having Structure (III)

6. The depot formulation according to claim 1 wherein the $X_{50}$ value of the crystals is from 10 to 170 microns.

7. The depot formulation according to claim 6 wherein the $X_{50}$ value of the crystals is from 15 to 70 microns.

8. The depot formulation according to claim 2 which additionally comprises an additional ingredient selected from the group consisting of a surfactant, solubilizer, emulsifier, preservative, isotonicity agent, dispersing agent, wetting agent, filler, solvent, buffer, stabilizer, lubricant, thickening agent, and combinations thereof.

9. The depot formulation according to claim 8 wherein the surfactant is selected from the group consisting of a sorbitan fatty acid ester, phosphatide, polyoxyethylated sorbitan monooleate, polyoxyalkylene derivatives of propylene glycol, polyoxyethylated fat, polyoxyethylated oleotriglyceride, linolizated oleotriglyceride, polyethylene oxide condensation products of fatty alcohol, and an alkylphenol.

10. The depot formulation according to claim 9 wherein the surfactant is a polyoxyalkylene derivative of propylene glycol.

11. The depot formulation according to claim 8 wherein the concentration of surfactant is in the range of about 0.5 to about 10 mg/mL.

12. The depot formulation according to claim 8 wherein the thickening agent is selected from the group consisting of sodium carboxymethyl cellulose, hydroxypropyl cellulose, calcium carboxymethyl cellulose, and crosslinked carboxymethyl cellulose.

13. The depot formulation according to claim 12 wherein the thickening agent is sodium carboxymethylcellulose.

14. The depot formulation according to claim 8 wherein the concentration of thickening agent is in the range of about 2 to about 25 mg/mL.

15. The depot formulation according to claim 8 wherein the isotonicity agent is selected from the group consisting of salts such as sodium chloride; sugars such as dextrose, mannitol, and lactose.

16. The depot formulation according to claim 15 wherein the isotonicity agent is mannitol.

17. The depot formulation according to claim 1 wherein the crystals are in a form selected from the group consisting of needles, trigonal forms, tetragonal forms, flat rod shaped, cubes, parallelepipeds, and plate-like needles.

* * * * *